United States Patent
Wang

(10) Patent No.: US 10,338,608 B2
(45) Date of Patent: Jul. 2, 2019

(54) UNMANNED AERIAL VEHICLE AND WATER SAMPLING METHOD THEREOF

(71) Applicant: SZ DJI TECHNOLOGY CO., LTD., Shenzhen (CN)

(72) Inventor: Mingyu Wang, Shenzhen (CN)

(73) Assignee: SZ DJI TECHNOLOGY CO., LTD., Shenzhen (CN)

( * ) Notice: Subject to any disclaimer, the term of this patent is extended or adjusted under 35 U.S.C. 154(b) by 26 days.

(21) Appl. No.: 15/604,894

(22) Filed: May 25, 2017

(65) Prior Publication Data

US 2017/0261998 A1    Sep. 14, 2017

Related U.S. Application Data

(63) Continuation of application No. PCT/CN2014/092576, filed on Nov. 28, 2014.

(51) Int. Cl.
*G01N 1/02* (2006.01)
*G01N 1/10* (2006.01)
(Continued)

(52) U.S. Cl.
CPC ............ *G05D 1/102* (2013.01); *B64C 25/54* (2013.01); *B64C 39/024* (2013.01); *G01N 1/12* (2013.01); *G01N 1/14* (2013.01); *G01S 19/49* (2013.01); *G05D 1/0011* (2013.01); *G05D 1/042* (2013.01); *B64C 2201/027* (2013.01);
(Continued)

(58) Field of Classification Search
CPC ...... G01N 1/12; G01N 1/14; G01N 2001/021; G01N 2001/1031; G01N 33/18; B64C 39/024; B64C 25/54; B64C 2201/146; G01S 15/88; G01S 19/42; G01S 19/49;
(Continued)

(56) References Cited

U.S. PATENT DOCUMENTS 3,748,867 A    7/1973 Hamri
6,809,648 B1 *  10/2004 Fleming ................ G01K 13/02
                                              340/601
(Continued)

FOREIGN PATENT DOCUMENTS

CN    101592649 A    12/2009
CN    101866180 A    10/2010
(Continued)

OTHER PUBLICATIONS

The World Intellectual Property Organization (WIPO) International Search Report for PCT/CN2014/092576 dated Aug. 20, 2015 6 Pages.

*Primary Examiner* — Atul Trivedi
(74) *Attorney, Agent, or Firm* — Anova Law Group, PLLC

(57) ABSTRACT

A water sampling method includes acquiring, by an unmanned aerial vehicle, a sampling depth at which a water sample is to be taken. The sampling depth is sent by a portable electronic device or is a preset default depth. The method further includes calculating a descending distance based on the sampling depth and a distance between the unmanned aerial vehicle and a water surface, controlling the water sampler to descend for the descending distance, sampling, by the water sampler, a water sample, and sending a sampling result to a ground station or the portable electronic device.

20 Claims, 8 Drawing Sheets

(51) Int. Cl.
*G01N 1/12* (2006.01)
*G01N 1/14* (2006.01)
*G05D 1/00* (2006.01)
*G05D 1/04* (2006.01)
*G05D 1/10* (2006.01)
*B64C 25/54* (2006.01)
*B64C 39/02* (2006.01)
*G01N 33/18* (2006.01)
*G01S 15/88* (2006.01)
*G01S 19/42* (2010.01)
*G01S 19/49* (2010.01)

(52) U.S. Cl.
CPC .... *B64C 2201/108* (2013.01); *B64C 2201/12* (2013.01); *B64C 2201/146* (2013.01); *G01N 33/18* (2013.01); *G01N 2001/021* (2013.01); *G01N 2001/1031* (2013.01); *G01S 15/88* (2013.01); *G01S 19/42* (2013.01); *G05D 1/0016* (2013.01)

(58) Field of Classification Search
CPC .... G05D 1/0011; G05D 1/0016; G05D 1/042; G05D 1/102
USPC .......................................................... 701/2
See application file for complete search history.

(56) References Cited

U.S. PATENT DOCUMENTS

| | | | | |
|---|---|---|---|---|
| 8,909,391 | B1* | 12/2014 | Peeters | G05D 1/0027 701/2 |
| 9,174,733 | B1* | 11/2015 | Burgess | B64D 1/12 |
| 9,262,929 | B1* | 2/2016 | Roy | G08G 5/0034 |
| 9,440,718 | B1* | 9/2016 | Tang | B63G 8/001 |
| 9,563,203 | B2 | 2/2017 | Davoodi | G05D 1/0088 |
| 9,665,094 | B1* | 5/2017 | Russell | G05D 1/00 |
| 9,791,862 | B1* | 10/2017 | Connor | G05D 1/0206 |
| 9,817,396 | B1* | 11/2017 | Takayama | G05D 1/0038 |
| 10,011,352 | B1* | 7/2018 | Dahlstrom | B64C 39/022 |
| 10,023,323 | B1* | 7/2018 | Roberts | B64D 43/00 |
| 10,054,104 | B1* | 8/2018 | Cote | F03B 13/20 |
| 10,059,467 | B2* | 8/2018 | Wang | B64F 1/00 |
| 10,131,428 | B1* | 11/2018 | Sopper | B64C 27/08 |
| 2007/0276552 | A1* | 11/2007 | Rodocker | B62D 57/00 701/2 |
| 2010/0005857 | A1* | 1/2010 | Zhang | B63C 11/48 73/29.02 |
| 2010/0131133 | A1* | 5/2010 | Koda | G05D 1/0206 701/21 |
| 2010/0292873 | A1* | 11/2010 | Duggan | G05D 1/0061 701/11 |
| 2012/0289103 | A1* | 11/2012 | Hudson | F42B 19/00 440/38 |
| 2014/0146303 | A1 | 5/2014 | Mitchell | |
| 2014/0160886 | A1* | 6/2014 | Muyzert | G01V 1/3843 367/16 |
| 2014/0165898 | A1* | 6/2014 | Cierpka | G01S 15/89 114/312 |
| 2014/0237951 | A1* | 8/2014 | Szydlowski | A23L 2/00 53/473 |
| 2015/0266576 | A1* | 9/2015 | Hobbart | B60F 5/006 244/2 |
| 2015/0268136 | A1* | 9/2015 | Detweiller | G01N 1/14 73/864.34 |
| 2015/0346726 | A1* | 12/2015 | Davoodi | B63B 22/24 701/21 |
| 2016/0221683 | A1* | 8/2016 | Roberts | B64D 27/02 |
| 2016/0286128 | A1* | 9/2016 | Zhou | H04N 5/23248 |
| 2016/0376000 | A1* | 12/2016 | Kohstall | B64C 37/00 114/313 |
| 2017/0022728 | A1* | 1/2017 | Simik | C02F 1/001 |
| 2017/0083018 | A1* | 3/2017 | Womble | A01K 27/009 |
| 2017/0127652 | A1* | 5/2017 | Shen | A01K 15/021 |
| 2017/0240257 | A1* | 8/2017 | Brandt | B63G 8/001 |
| 2017/0261998 | A1* | 9/2017 | Wang | G01N 1/14 |
| 2017/0293302 | A1* | 10/2017 | Johnson | B63B 35/00 |
| 2017/0313332 | A1* | 11/2017 | Paget | B61L 27/0077 |
| 2017/0365150 | A1* | 12/2017 | Bennett | A01D 34/008 |
| 2018/0073265 | A1* | 3/2018 | Goldenberg | E04H 4/1654 |
| 2018/0156770 | A1* | 6/2018 | Saez | B64C 39/02 |
| 2018/0157259 | A1* | 6/2018 | Myslinski | G08B 21/18 |
| 2018/0208309 | A1* | 7/2018 | Wang | B64C 25/56 |
| 2019/0004512 | A1* | 1/2019 | Liu | H04N 5/247 |
| 2019/0023392 | A1* | 1/2019 | Micros | B64C 33/025 |

FOREIGN PATENT DOCUMENTS

| | | |
|---|---|---|
| CN | 102120088 A | 7/2011 |
| CN | 102407925 A | 4/2012 |
| CN | 102591355 A | 7/2012 |
| CN | 103235602 A | 8/2013 |
| CN | 103543751 A | 1/2014 |
| CN | 103809600 A | 5/2014 |
| CN | 203601574 U | 5/2014 |
| CN | 103869255 A | 6/2014 |
| CN | 103983474 A | 8/2014 |
| CN | 104122117 A | 10/2014 |
| CN | 104155297 A | 11/2014 |
| JP | S5587073 A | 7/1980 |

* cited by examiner

UNMANNED AERIAL VEHICLE AND WATER SAMPLING METHOD THEREOF

CROSS-REFERENCE TO RELATED APPLICATION

This is a continuation application of International Application No. PCT/CN2014/092576, filed on Nov. 28, 2014, the entire contents of which are incorporated herein by reference.

TECHNICAL FIELD

The present disclosure relates to a water sampling system for sampling a water sample and a water sampling method thereof.

BACKGROUND

In monitoring of environmental pollution and investigation of water body pollution, to truly reflect the status of water pollution, a representative water sample can be sampled. At present, water quality monitoring is away from the shore and in an occasion where manual water quality sampling is not easy, and the sampling personnel is required to take a boat or motorboat to a sampling site to sample the water quality. However, such a method evidently has its shortcomings. On the one hand, the sampling personnel needs to take a boat or motorboat, which requires much time and effort, and sometimes, a task can be accomplished only through multi-person cooperation. On the other hand, the boat or motorboat taken by the sampling personnel is driven to the sampling site, which may contaminate water quality of the sampling site and lead to inaccurate research results.

SUMMARY OF THE DISCLOSURE

An objective of the present disclosure is to provide an unmanned aerial vehicle for sampling a water sample and a water sampling method thereof which have a low cost, save time and effort and can ensure that water quality of a sampling site is not contaminated.

An embodiment of the present disclosure is implemented as a water sampling method including acquiring, by an unmanned aerial vehicle, a sampling depth at which a water sample is to be taken. The sampling depth is sent by a portable electronic device or is a preset default depth. The method further includes calculating a descending distance based on the sampling depth and a distance between the unmanned aerial vehicle and a water surface, controlling the water sampler to descend for the descending distance, sampling, by the water sampler, a water sample, and sending a sampling result to a ground station or the portable electronic device.

The method further includes receiving, by the unmanned aerial vehicle, position information of a sampling site, and flying to the sampling site based on the position information of the sampling site.

Receiving the position information of the sampling site includes receiving the position information of the sampling site sent by the portable electronic device selected from a satellite map displayed on the portable electronic device or input into the portable electronic device.

The method further includes flying to a sampling site under a control of a remote controller.

Acquiring the sampling depth includes acquiring a depth value input into the portable electronic device and sent by the portable electronic device to the unmanned aerial vehicle.

The method further includes floating on the water surface through a floating board attached to the unmanned aerial vehicle, such that the distance between the unmanned aerial vehicle and the water surface is zero.

The preset delimit depth is about 0.4 m to about 1 m underwater.

The method further includes measuring, by a distance sensor attached to the unmanned aerial vehicle, the distance between the unmanned aerial vehicle and the water surface.

The distance sensor is an ultrasonic sensor or a barometer.

The method further includes controlling a lifting device to drive the water sampler to descend by the descending distance.

The method further includes: flying, by the unmanned aerial vehicle, to a return point or flying to a next sampling site.

The method further includes: calculating remaining power of the unmanned aerial vehicle before takeoff, and when the remaining power is not enough for the unmanned aerial vehicle to fly to the return point after sampling of the water sample, prohibiting the takeoff.

The method further includes: calculating remaining power of the unmanned aerial vehicle before takeoff, and when the remaining power is not enough for the unmanned aerial vehicle to fly to the sampling site, prohibiting the takeoff.

The unmanned aerial vehicle and the ground station or the portable electronic device establish communication through a 3G network, a 4G network, a 5G network, WI-FI, or NFC.

When the acquired depth at which the water sample is to be taken is the preset default value, after the unmanned aerial vehicle descends or ascends to a position at a distance of a preset first height from a water surface, the water sampler is controlled to descend a preset first descending value to cause the water sampler to arrive at the depth at which the water sample is to be taken, and the first descending value is equal to the sum of the first height and the depth at which the water sample is to be taken.

An embodiment of the present disclosure is implemented as a water sampling system including an unmanned aerial vehicle and a water sampler coupled to the unmanned aerial vehicle. The water sampler is configured to ascend and descend relative to the unmanned aerial vehicle and to sample a water sample. The unmanned aerial vehicle is configured to acquire a sampling depth at which a water sample is to be taken. The sampling depth is sent by a portable electronic device or is a preset default depth. The unmanned aerial vehicle is further configured to calculate a descending distance based on the sampling depth and a distance between the unmanned aerial vehicle and a water surface, and control the water sampler to descend for the descending distance.

The unmanned aerial vehicle comprises a signal transceiver configured to receive position information of a sampling site. The unmanned aerial vehicle is further configured to fly to the sampling site based on the position information of the sampling site. The signal transceiver is further configured to send a sampling result to the portable electronic device or a ground station.

The signal transceiver is configured to receive the position information of the sampling site sent by the portable electronic device selected from a satellite map displayed on the portable electronic device or input into the portable electronic device.

The signal transceiver is further configured to receive a control signal from a remote controller, and the unmanned aerial vehicle is configured to fly to the sampling site under a control of the remote controller.

The transceiver is further configured to receive a depth value input into and sent by the portable electronic device as the sampling depth at which the water sample is to be taken.

The unmanned aerial vehicle comprises a floating board and is configured to float on the water surface through the floating board, such that the distance between the unmanned aerial vehicle and the water surface is zero.

The preset delimit depth is about 0.4 m about 1 m underwater.

The unmanned aerial vehicle comprises a distance sensor configured to measure the distance between the unmanned aerial and the water surface.

The distance sensor is an ultrasonic sensor a barometer.

The unmanned aerial vehicle further comprises a lifting device configured to drive the water sampler to ascend or descend relative to the unmanned aerial vehicle. The unmanned aerial vehicle is further configured to control the lifting device to drive the water sampler to descend by the descending distance.

The lifting device includes a rotary rolling member and a connecting rope, and the unmanned aerial vehicle controls the rotary rolling member to rotate to cause the connecting rope to drive the water sampler ascend and descend relative to the unmanned aerial vechicle.

The connecting rope is made of hard rubber.

The unmanned aerial vehicle further includes a memory in which a sampling result by the water sampler is stored.

The unmanned aerial vehicle is further used for transmitting the sampling result stored in the memory to the ground station or the portable electronic device throng a 3G network, a 4G network, a 5G network, WI-FI, or NFC.

The unmanned aerial vehicle sends the sampling result by the water sampler to the portable electronic device or a ground station in real time, or the water sampler sends the sampling result to the portable electronic device or the ground station in real time.

The unmanned aerial vehicle is further used for calculating remaining power of the unmanned aerial vehicle before takeoff, and when the remaining power is not enough for the unmanned aerial vehicle to fly to the return point after sampling of the water sample, prohibiting the takeoff.

The unmanned aerial vehicle is further used for calculating remaining power of the unmanned aerial vehicle before takeoff, and when the remaining power is not enough for the unmanned aerial vehicle to fly to the sampling site, prohibiting the takeoff.

An embodiment of the present disclosure is implemented as follows: a water sampling method based on an unmanned aerial vehicle provided thereon with a water sample collector and a water sampler, including:

flying to a sampling site;

pumping, by the water sample collector, a water sample;

sampling, by the water sampler, the water sample pumped by the water ample collector; and sending a sampling result to a ground station or a portable electronic device.

The water sample collector includes a floating board, a water pump, a reservoir, a first connecting pipe, and a second connecting pipe. The water pump and the reservoir are disposed on the floating board. The water sampler is disposed in the reservoir. The water pump and the reservoir are connected through the first connecting pipe. One end of the second connecting pipe is connected to the water pump. The floating board is connected to the unmanned aerial vehicle, and the pumping, by the water sample collector, of a water sample comprises:

based on a distance between the unmanned aerial vehicle and a water surface, descending the floating board, by the unmanned aerial vehicle such that the floating board floats at a water surface; and pumping, by the water pump, the water sample, to the reservoir.

The sampling, by the water sampler, of the water sample pumped by the water sample collector comprises:

sampling, by the water sampler, the water sample in the reservoir.

The sending a sampling result to a ground station or a portable electronic device comprises:

sending, by the water sampler, the sampling result to the unmanned aerial vehicle, and sending, by the unmanned aerial vehicle, the sampling result to the ground station or the portable electronic device; or sending, by the water sampler, the sampling result to the ground station or the portable electronic device directly.

The water sample collector includes a floating board, a water pump, a reservoir, a first connecting pipe, and a second connecting pipe. The water pump and the reservoir are disposed on the floating board. The water sampler is disposed in the reservoir. The water pump and the reservoir are connected through the first connecting pipe. One end of the second connecting pipe is connected to the water pump. The floating board is connected to the unmanned aerial vehicle through a lifting device, and the pumping, by the water sample collector, a water sample comprises:

based on a distance between the unmanned aerial vehicle and a water surface, descending the floating board, by the lifting device such that the floating board floats at a water surface; and pumping, by the water pump, the water sample to the reservoir.

The method further includes: flying, by the unmanned aerial vehicle, to a return point or flying to a next sampling site.

The method further includes: calculating remaining power of the unmanned aerial vehicle before takeoff, and when the remaining power is not enough for the unmanned aerial vehicle to fly to the return point after sampling of the water sample, prohibiting the takeoff.

The method further includes: calculating remaining power of the unmanned aerial vehicle before takeoff, and when the remaining power is not enough for the unmanned aerial vehicle to fly to the sampling site, prohibiting the takeoff.

The method further includes: receiving, by the unmanned aerial vehicle, position information of the sampling site, and flying, by the unmanned aerial vehicle, to the sampling site autonomously based on the position information of the sampling site.

The position information of the sampling site is sent by the portable electronic device displaying a satellite map, the sampling site may be selected from the satellite map or input into the portable electronic device, and the portable electronic device sends position information of the selected sampling site to the unmanned aerial vehicle.

The unmanned aerial vehicle flies to the sampling site under the control of a remote controller.

A distance between the unmanned aerial vehicle and a water surface is measured through a distance sensor on the unmanned aerial vehicle.

The distance sensor is an ultrasonic sensor or a barometer.

An implementation mode of the present disclosure is as follows: an unmanned aerial vehicle for sampling a water sample, wherein the unmanned aerial vehicle is provided thereon with a water sample collector and a water sampler. The unmanned aerial vehicle is used for carrying the water sample collector and the water sampler to fly to a sampling site. The water sample collector is used for pumping a water sample. The water sampler is used for sampling the water sample pumped by the water sample collector, and the unmanned aerial vehicle or the water sampler sends a sampling result to a ground station or a portable electronic device.

The water sample collector includes a floating board, a water pump, a reservoir, a first connecting pipe, and a second connecting pipe. The water pump and the reservoir are disposed on the floating board. The water sampler is disposed in the reservoir. The water pump and the reservoir are connected through the first connecting pipe. One end of the second connecting pipe is connected to the water pump. The floating board is connected to the unmanned aerial vehicle. The floating board is used for causing the water sample collector to float at a water surface. The water pump is used for pumping the water sample to the reservoir, and the water sampler samples the water sample in the reservoir.

The water pump is a peristaltic pump.

The reservoir is provided with a water outlet.

Both the first connecting pipe and the second connecting pipe are silicone tubes.

The other end of the second connecting pipe is provided with a filter.

The unmanned aerial vehicle is further used for calculating remaining power of the unmanned aerial vehicle before takeoff, and when the remaining power is not enough fur the unmanned aerial vehicle to fly to the sampling site, prohibiting the takeoff.

The unmanned aerial vehicle includes a signal transceiver for receiving position information of the sampling site, and the unmanned aerial vehicle flies to the sampling site autonomously based on the position information of the sampling site.

Position information of the sampling site is sent by the portable electronic device displaying a satellite map, the sampling site may be selected from the satellite map or input into the portable electronic device, and the portable electronic device sends position information of the selected sampling site to the signal transceiver.

The signal transceiver is further used for receiving a control signal of a remote controller, and the unmanned aerial vehicle flies to the sampling site under the control of the remote controller.

The unmanned aerial vehicle is mounted with a distance sensor.

The distance sensor is an ultrasonic sensor or a barometer.

The water sample collector is connected to the unmanned aerial vehicle through a lifting device which includes at least one rotary milling member and at least one connecting rope, and the unmanned aerial vehicle controls the rotary rolling member to rotate to cause the connecting rope to drive the water sampler to ascend and descend relative to the unmanned aerial vehicle and to cause the floating board to float at the water surface.

The water sample collector is fixedly connected onto a landing gear of the unmanned aerial vehicle.

The unmanned aerial vehicle further includes a memory in which a sampling result by the water sampler is stored.

The unmanned aerial vehicle is further used for transmitting the sampling result stored in the memory to the around station or the portable electronic device through a 3G network, a 4G network, a 5G network, WI-FI, or NFC.

The unmanned aerial vehicle is further used fur calculating remaining power of the unmanned aerial vehicle before takeoff, and when the remaining power is not enough for the unmanned aerial vehicle to fly to the return point after sampling of the water sample, prohibiting the takeoff.

The unmanned aerial vehicle is further used for calculating remaining power of the unmanned aerial vehicle before takeoff, and when the remaining power is not enough for the unmanned aerial vehicle to fly to the sampling site, prohibiting the takeoff.

Relative to the prior art, the unmanned aerial vehicle of the present disclosure is used for sampling a water sample, which can reduce the cost as comparing to taking a boat or motorboat by the sampling personnel, and at the same time, can prevent the boat or motorboat from contaminating water quality of a sampling site, thus ensuring that the water quality of the sampling site is not contaminated. In this way, the unmanned aerial vehicle of the present disclosure can make a water sampler precisely descend to a predetermined depth.

DETAILED DESCRIPTION OF THE EMBODIMENTS

The technical solution in embodiments of the present disclosure is clearly and completely described below with reference to the accompanying drawings of the embodiments of the present disclosure. It is apparent that the embodiments described are merely some embodiments of the present disclosure instead of all the embodiments. Based on the embodiments in the present disclosure, all other embodiments obtained by persons of ordinary skill in the art without making creative efforts all fall within the protection scope of the present disclosure.

Implementation or the present disclosure is described in detail below in combination with specific implementation modes.

Figure 1:
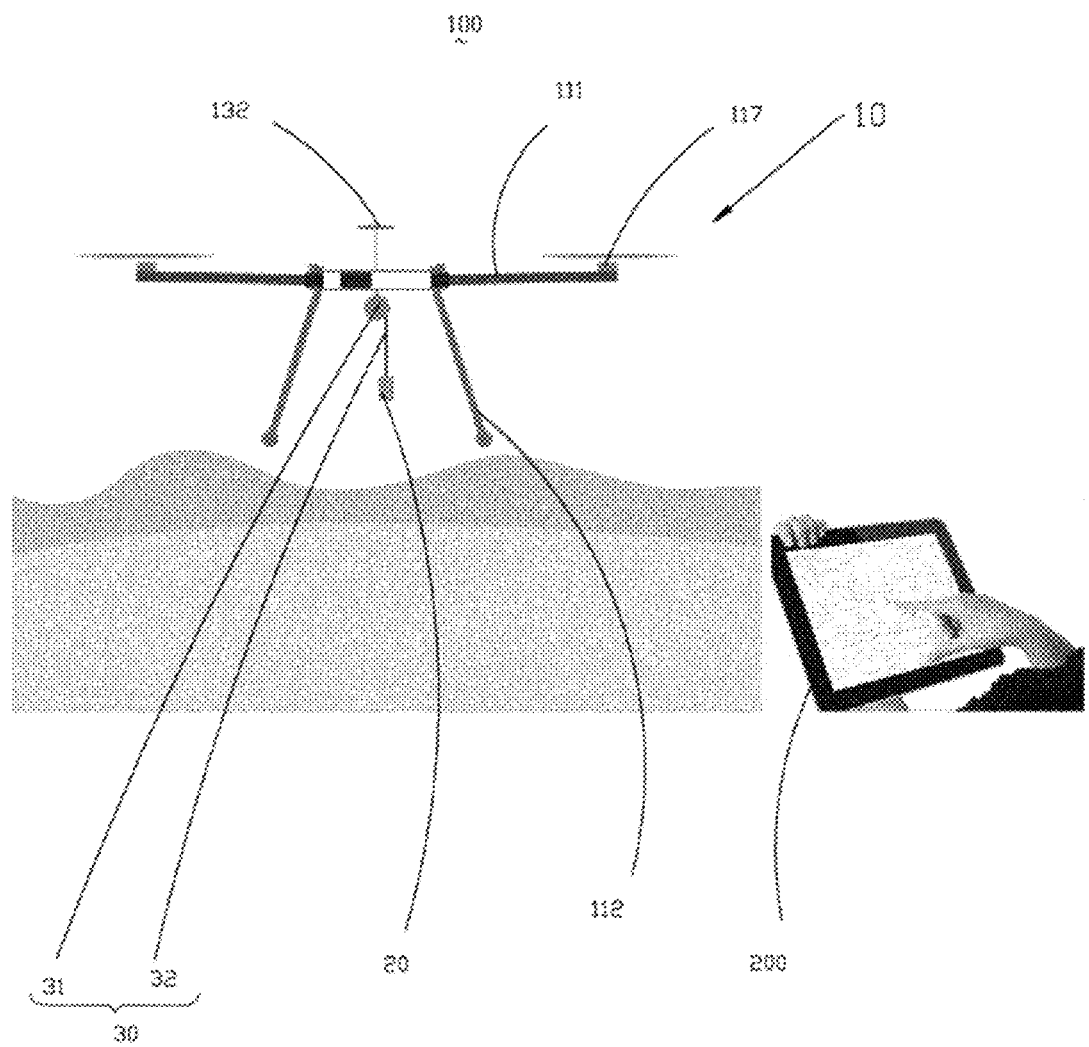
FIG. 1 is a use state diagram of a water sampling system according to a first implementation mode of the present disclosure.
Figure 2:
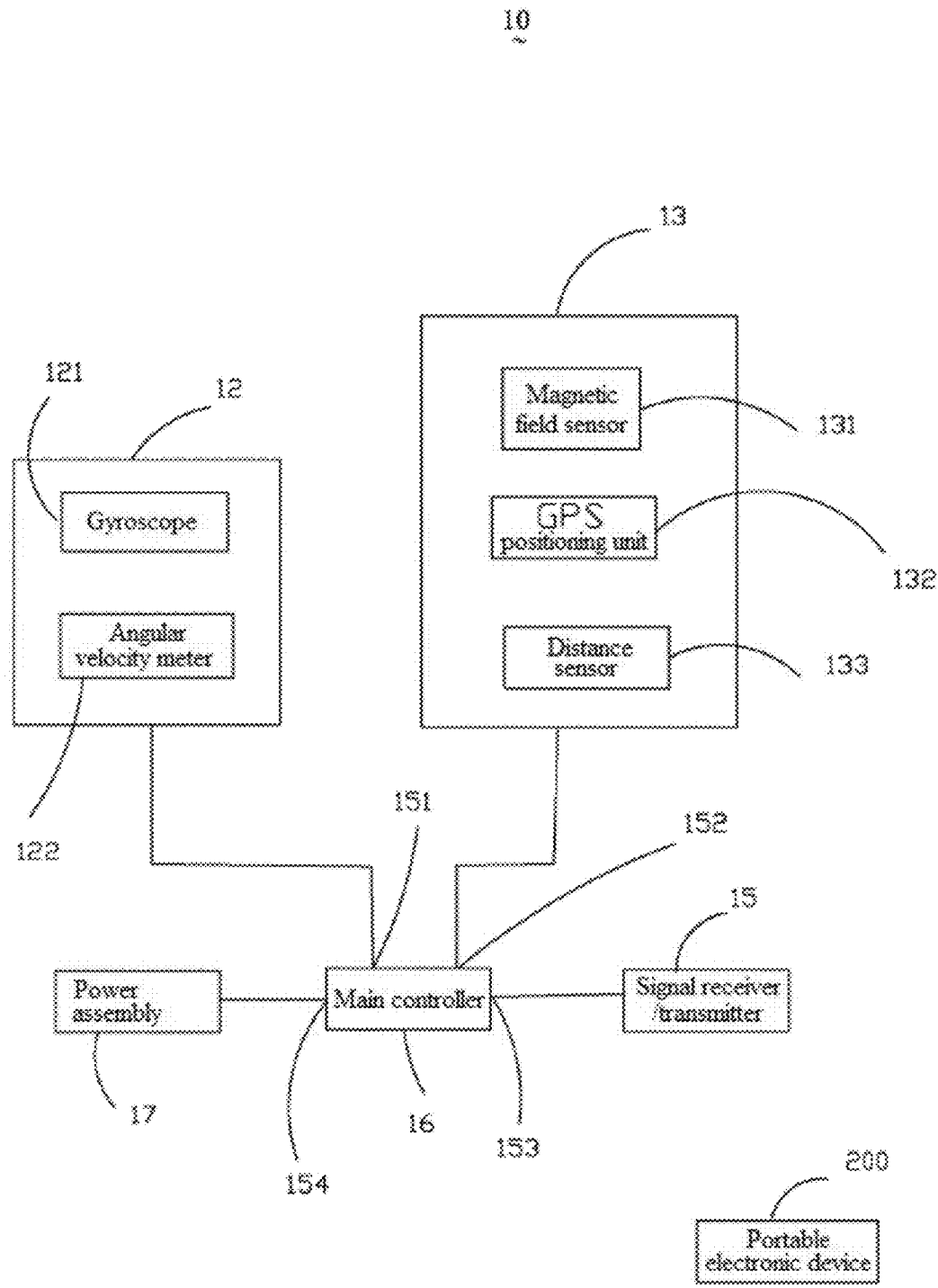
FIG. 2 is a schematic diagram of a frame of the unmanned aerial vehicle in FIG. 1.

Referring to FIGS. 1-2 together, a water sampling system 100 according to the present disclosure includes an unmanned aerial vehicle 10, a water sampler 20 disposed on the unmanned aerial vehicle 10, and a lifting device 30 disposed on the unmanned aerial vehicle 10 and used for enabling the water sampler 20 to ascend and descend relative to the unmanned aerial vehicle 10.

In this embodiment, the unmanned aerial vehicle 10 is an unmanned aircraft, which includes a vehicle body, an Inertial Measurement Unit (IMU) 12, a positioning assembly 13, a memory 14, a signal transceiver 15, a main controller 16, and a power assembly 17. The IMU 12, the positioning assembly 13, the memory 14, the signal transceiver 15, the main controller 16, and the power assembly 17 are all mounted to the vehicle body.

The vehicle body includes a body portion 111 and two landing gears 112 which are used for supporting the body portion 111 and can ascend and descend relative to the body portion 111.

The IMU 12 is mounted in the body portion 111, and the IMU 12 is used for measuring attitude information of the unmanned aerial vehicle 10. The IMU 12 includes a gyroscope 121 and an angular velocity meter 122. The main controller 16 is electrically connected with the IMU 12 for detecting operational data of the gyroscope 121 and the angular velocity meter 122.

The positioning assembly 13 includes a magnetic field sensor 131, a GPS positioning unit 132, and a distance sensor 133. In this implementation mode, the magnetic field sensor 131 is a compass, and the distance sensor 133 is a barometer. The positioning assembly 13 is electrically connected to the main controller 16. The main controller 16 is further used for detecting operational data of the magnetic field sensor 131 and the GPS positioning unit 132. It can be understood that, in other implementation modes, the distance sensor 133 may also be an ultrasonic sensor or the like, which is not limited to this implementation mode.

The type of the memory 14 is an SD card, an MMC card, or a FLASH memory. In some embodiments, as a 4G SD card has a relatively low cost, the memory 14 in this embodiment is a 4G SD card, which can thus reduce the cost of the product.

The signal transceiver 15 is used for receiving a remote control signal and a GPS positioning signal indicating where the unmanned aerial vehicle is to fly and for sending the received remote control signal and the GPS positioning signal indicating where the unmanned aerial vehicle is to fly to the main controller 16. In this embodiment, the GPS positioning signal indicating where the unmanned aerial vehicle is to fly may be sent by a portable electronic device 200, and in this embodiment, the portable electronic device 200 is an iPad, an iPhone or the like. In other embodiments, the portable electronic device 200 may also be a ground station.

The signal transceiver 15 is further used for transmitting a sampling result of the water sampler 20 to the portable electronic device 200.

In this embodiment, the main controller 16 may be implemented with an 8-bit or 32-bit MCU, and may have an SPI interface and/or SDIO interface, and PWM output and/or DAC output capabilities. As the cost of the existing 8-bit or 32-bit MCU is relatively low, when the controller 16 in this embodiment is implemented with an 8-bit or 32-bit MCU, the cost of the product can be further reduced. The main controller 16 includes a first signal input interface 151, a second signal input interface 152, a third signal input interface 153, and a signal output interface 154. The first signal input interface 151 is electrically connected with the signal transceiver 15 through an SPI protocol or an SDIO protocol. Specifically, the main controller 16 and the signal receiver 15 are electrically connected with each other through a communication manner such as 4-line SPI, 6-line SIDO-4bit or 4-line SIDO-4bit. The second signal input interface 152 is electrically connected with the positioning assembly 13. The third signal input interface 153 is electrically connected with the signal receiver 15. The signal output interface 154 is electrically connected with the power assembly 17.

The main controller 16 is used for extracting operational data of the gyroscope 121, the angular velocity meter 122, the magnetic field sensor 131, and the GPS positioning unit 132. The main controller 16 is further used for controlling the power assembly 17.

It can be understood that the main controller 16 may also be set according to actual demands, which is not limited to this embodiment.

In this embodiment, the power assembly 17 includes a plurality of drive motors 171. In this embodiment, each of the drive motors 171 is electrically connected to an electronic speed control (ESC). Each electronic speed control is electrically connected to the main controller 16. The ESC is used for receiving a control signal of the main controller 16, and controlling a rotational, speed, of the drive motor 171.

In this embodiment, the water sampler 20 is a portable multi-parameter water quality sampling instrument, and parameters of the water quality that the water sampler can sample include: dissolved oxygen, chloride ions, pH, ORP, TDS, electrical conductivity, dissolved oxygen, turbidity, COD, TOC, residual chlorine, chlorine dioxide, hardness, volatile phenol, ammonia nitrogen, total phosphorus, total nitrogen, fluoride, cyanide, chromium, manganese, and other metal ions, phosphate, sulfate, nitrate, surface active agent, chromaticity, absorbance, and the like.

In this embodiment, the lifting device 30 includes a rotary rolling member 31 and a connecting rope 32. The rotary rolling member 31 is a driving wheel. In this embodiment, the connecting rope 32 is made of a hard hose. The connecting rope 32 is disposed between the rotary rolling member 31 and the water sampler 20.

It can be understood that, in other embodiments, the lifting device 30 may also be another structural design, as long as the lifting device can drive the water sampler 20 to ascend and descend relative to the unmanned aerial vehicle 10, which is not limited to this embodiment.

Figure 3:
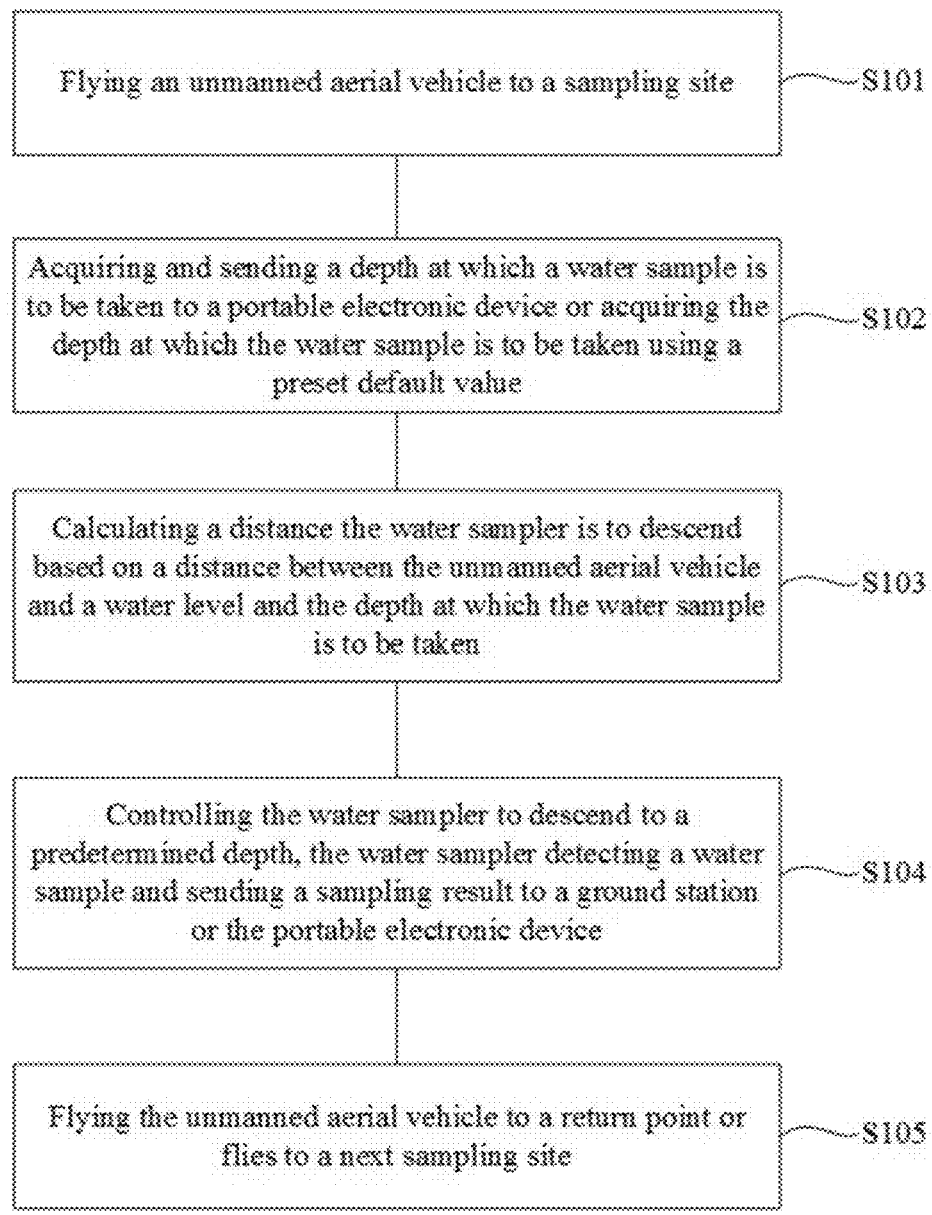
FIG. 3 is a flow chart of a water sampling method according to the first implementation mode of the present disclosure.

Referring to FIG. 3, a water sampling method according to a first implementation mode of the present disclosure includes the following steps:

S101: The unmanned aerial vehicle 10 flies to a sampling site.

In this embodiment, the signal transceiver 15 on the unmanned aerial vehicle 10 receives position information of a sampling site sent by the portable electronic device 200. Specifically, the portable electronic device 200 is wirelessly connected with the signal transceiver 15 of the unmanned aerial vehicle 10 through a wi-fi technology, a NFC technology, a wireless communication network (a 3G, 4G, or 5G network) or the like. The portable electronic device 200 displays a satellite map. An operator can select the sampling site from the satellite map or input the sampling site, and the portable electronic device 200 sends position information of the selected sampling site to the signal transceiver 15 of the unmanned aerial vehicle 10. The signal transceiver 15, upon receipt of the position information of the sampling site, sends the position information to the main controller 16. The main controller 16 controls the unmanned aerial vehicle 10 to fly to the sampling site autonomously based on a current position of the unmanned aerial vehicle 10 positioned by the GPS positioning unit 132 of the positioning assembly 13 and the position information of the sampling site received by the signal receiver 15.

It can be understood that the manner that the unmanned aerial vehicle 10 flies to the sampling site is not limited to this implementation mode, and in other embodiments, the unmanned aerial vehicle 10 may also fly to the sampling site under the control of a remote controller. The remote controller is wirelessly connected with the signal transceiver 15, and the signal receiver 15 receives a remote control signal of the remote controller.

In this embodiment, the unmanned aerial vehicle 10 includes a battery (not shown) for providing electric energy for the power assembly 17 of the unmanned aerial vehicle 10, and the unmanned aerial vehicle 10 may be provided with the water sampler 20 of a different model. Before takeoff, the operator may input the model of the water sampler 20 into the portable electronic device 200. The unmanned aerial vehicle 10 may calculate whether remaining power of the unmanned aerial vehicle 10 is enough for the unmanned aerial vehicle to fly to the sampling site and fly to a predetermined point after acquisition of the water sample based on the power of the battery that the unmanned aerial vehicle 10 carries, the weight of the water sampler 20, a distance between a takeoff point of the unmanned aerial vehicle 10 and the sampling site and a distance between the sampling site and a return point. Only when the remaining power is enough for the unmanned aerial vehicle 10 to fly to the sampling site and fly to the predetermined point after taking the water sample, can the unmanned aerial vehicle 10 take off. Otherwise, takeoff is prohibited. The unmanned aerial vehicle 10 will send the information to the portable electronic device 200 and prompt the operator through the portable electronic device 200.

In other implementation modes, remaining power of the unmanned aerial vehicle 10 can be calculated before takeoff, and when the residual power is not enough for the unmanned aerial vehicle 10 to fly to the sampling site, takeoff is prohibited.

S102: A depth at which a water sample is to be taken is acquired from a portable electronic device, or the depth at which the water sampling is to be taken is acquired using a preset default value.

As stated above, the portable electronic device 200 and the signal transceiver 15 of the unmanned aerial vehicle 10 are in a wireless connection, and the operator can input the depth value at which the water sample is to be taken into the portable electronic device 200, and output the depth value at which the water sample is to be taken to the signal transceiver 15. It can be understood that, in other implementation modes, the depth at which the water sample is to be taken may also be a preset default value (for example, about 0.4 m to about 1 m underwater, such as about 0.5 m), which is stored in the memory 14.

S103: A distance at which the water sampler is to descend is calculated based on a distance between the unmanned aerial vehicle and a water surface and the depth at which the water sample is to be taken.

The distance sensor 133 measures a distance between the unmanned aerial vehicle 10 and a water surface, and the main controller 16 calculates a distance at which the water sampler 20 is to descend based on the distance between the unmanned aerial vehicle 10 and the water surface and the depth at which the water sample is to be taken.

S104: The water sampler is controlled to descend to a predetermined depth, and the water sampler samples a water sample and sends a sampling result to a ground station or the portable electronic device.

The main controller 16 controls the lifting device 30 to drive the water sampler 20 to descend to a predetermined depth based on the distance the water sampler 20 is to descend. Specifically, the main controller 16 controls the rotary rolling member 31 to rotate to cause the connections rope 32 to drive the water sampler 20 to descend to a predetermined depth underwater. In this embodiment, in the process of sampling water by the water sampler 20, the unmanned aerial vehicle 10 hovers, and the main controller 16 only needs to read a distance from the unmanned aerial vehicle 10 to the water surface while the unmanned aerial vehicle 10 is hovering after flying to the sampling site, as measured by the distance sensor 133. In other embodiments, the process of pumping the water sample by the water sampler may also be performed when the unmanned aerial vehicle 10 does not hover, and the main controller 16 reads the distance between the unmanned aerial vehicle 10 and the water surface in real time, as measured by the distance sensor 133, and controls the rotary rolling member 31 to rotate in real time, so as to adjust the connecting rope 32 in real time to drive the water sampler 20 to descend to the predetermined depth underwater. The sampling result may be stored in the memory 14, and the signal transceiver 15 is further used for sending the sampling result to the portable electronic device 200 or a ground station. It can be understood that a wireless transmitting device can also be directly disposed on the water sampler 20, and the sampling result may also be sent to the portable electronic device 200 or the ground station through the wireless transmitting device.

It can be understood that, in other implementation modes, the rotary rolling member 31 can also be controlled to rotate using other devices disposed on the unmanned aerial vehicle, which is not limited to this embodiment.

S105: The unmanned aerial vehicle flies to a return point or flies to a next sampling site.

After sampling of the water sample is completed, the unmanned aerial vehicle 10 flies to a return point. The return point may be a takeoff point of the unmanned aerial vehicle 10 or a return point oh the map displayed on the portable electronic device 200.

Figure 4:
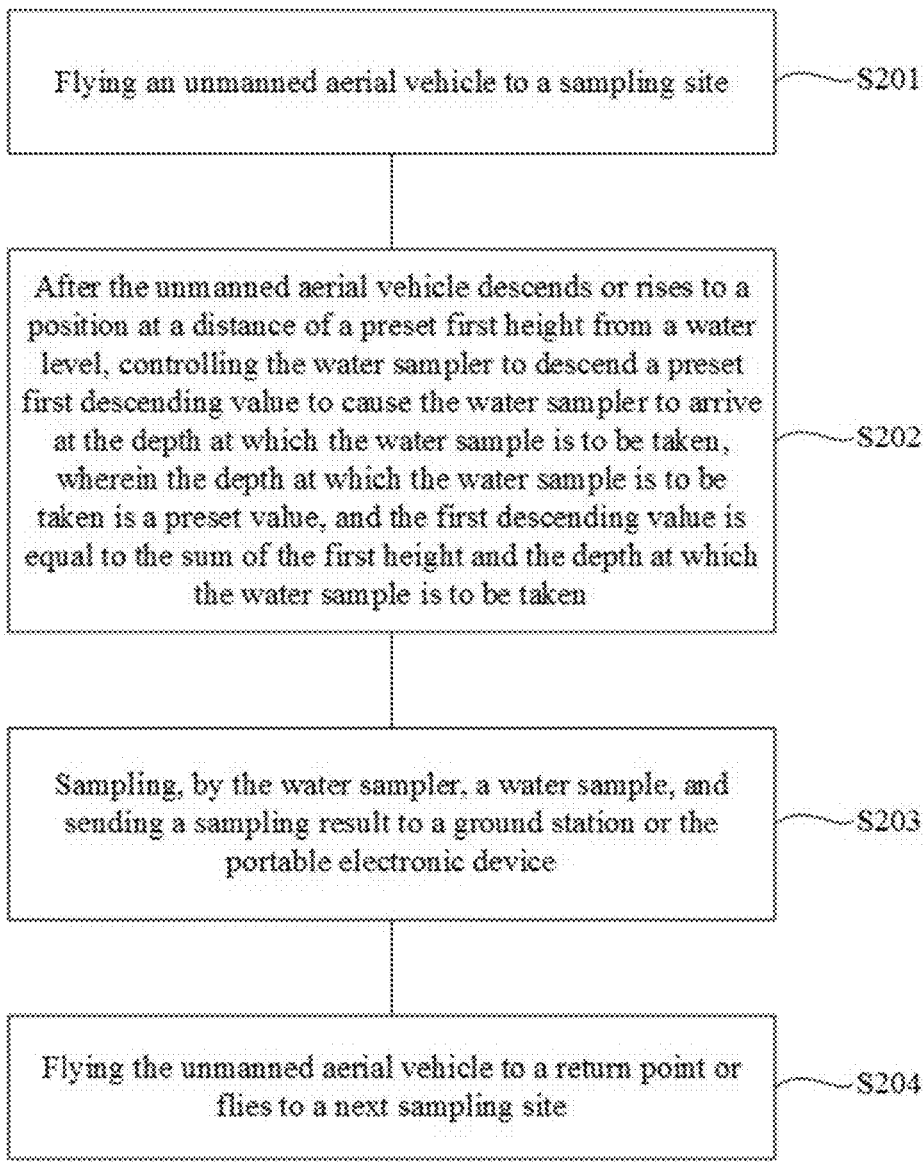
FIG. 4 is a flow chart of a water sampling method according to a second implementation mode of the present disclosure.

Referring to FIG. 4, a water sampling method according to a second implementation manner of the present disclosure includes the following steps:

S201: The unmanned aerial vehicle 10a flies to a sampling site.

In this embodiment, the signal transceiver 15 on the unmanned aerial vehicle 10 receives position information of the sampling site sent by the portable electronic device 200. Specifically, the portable electronic device 200 is wirelessly connected with the signal transceiver 15 of the unmanned aerial vehicle 10 through a wi-fi technology, a NFC technology, a wireless communication network or the like. The portable electronic device 200 displays a satellite map. An operator can select the sampling site from the satellite map or input the sampling site, and the portable electronic device 200 sends position information of the selected sampling site to the signal transceiver 15 of the unmanned aerial vehicle 10. The signal transceiver 15, upon receipt of the position information of the sampling site, sends the position information to the main controller 16. The main controller 16 controls the unmanned aerial vehicle 10 to fly to sampling site autonomously based on a current position of the unmanned aerial vehicle 10 positioned by the GPS positioning unit 132 of the positioning assembly 13 and the position information of the sampling site received by the signal transceiver 15.

It can be understood that the manner that the unmanned aerial vehicle 10 flies to the sampling site is not limited to this implementation mode, and in other embodiments, the unmanned aerial vehicle 10 may also fly to the sampling site under the control of a remote controller. The remote controller is wirelessly connected with the signal transceiver 15, and the signal receiver 15 receives a remote control signal of the remote controller.

In this embodiment, the unmanned aerial vehicle 10 includes a battery (not shown), for providing electric energy to the power assembly 17 of the unmanned aerial vehicle 10, and the unmanned aerial vehicle 10 may be provided with the water sampler 20 of a different model. Before takeoff, the operator may input the model of the water sampler 20 into the portable electronic device 200 The unmanned aerial vehicle 10 may calculate whether remaining power of the unmanned aerial vehicle 10 is enough for the unmanned aerial vehicle to fly to the sampling site and fly to a predetermined point after acquisition of the water sample based on the power of the battery that the unmanned aerial vehicle 10 carries, the weight of the water sampler 20, a distance between a takeoff point of the unmanned aerial vehicle 10 and the sampling site and a distance between a sampling site and a return point. Only when the remaining power is enough for the unmanned aerial vehicle 10 to fly to the sampling site and fly to the predetermined point after taking of the water sample, can the unmanned aerial vehicle 10 to take off. Otherwise, takeoff is prohibited. The unmanned aerial vehicle 10 will send the information to the portable electronic device 200 and prompt the operator through the portable electronic device 200.

In other implementation modes, remaining power of the unmanned aerial vehicle 10 can also be calculated before takeoff, and when the remaining power is not enough for the unmanned aerial vehicle 10 to fly to the sampling site, takeoff is prohibited.

S202: After the unmanned aerial vehicle descends or ascends to a position at a distance of a preset first height from a water surface, the water sampler 20 is controlled to descend a preset first descending value to cause the water sampler to arrive at the depth at which the water sample is to be taken. The depth at which the water sample is to be taken is a preset value, and the first descending value is equal to the sum of the first height and the depth at which the water sample is to be taken.

After the unmanned aerial vehicle 10 flies to the sampling site, the unmanned aerial vehicle 10 hovers at a first height from the water surface. Specifically, when flying to the sampling site, the unmanned aerial vehicle 10 descends to the first height when its height is higher than the first height; otherwise, it ascends to the first height. Then the main controller 16 controls the rotary rolling member 31 to rotate to cause the connecting rope 32 to drive the water sampler 20 to descend a preset first descending value and to cause the water sampler 20 to arrive at the depth at which the water sample is to be taken, which is a preset value, the first descending value being equal to the sum of the first height and the depth at which the water sample is to be taken, to enable the water sampler 20 to precisely descend to the depth at which the water sample is to be taken. In this embodiment, the first height value, the preset value of the depth at which the water sample is to be taken, and the first descending value are all stored in the memory 14.

S203: The water sampler 20 samples a water sample, and sends a sampling result to a ground station or the portable electronic device.

After the water sampler 20 performs sampling to obtain a sampling result of the water quality, the sampling result can be stored into the memory 14, and the signal transceiver 15 is further used for sending the sampling result to the portable electronic device 200 or a ground station. It can be understood that a wireless transmitting device can also be directly disposed on the water sampler 20, and the sampling result may also be sent to the portable electronic device 200 or the ground station through the wireless transmitting device.

S204: The unmanned aerial vehicle 10a flies to a return point or flies to a next sampling site.

After sampling of the water sample is completed, the unmanned aerial vehicle 10 flies to a return point. The return point may be a takeoff point of the unmanned aerial vehicle 10 or a return point on the map displayed on the portable electronic device 200.

Figure 5:
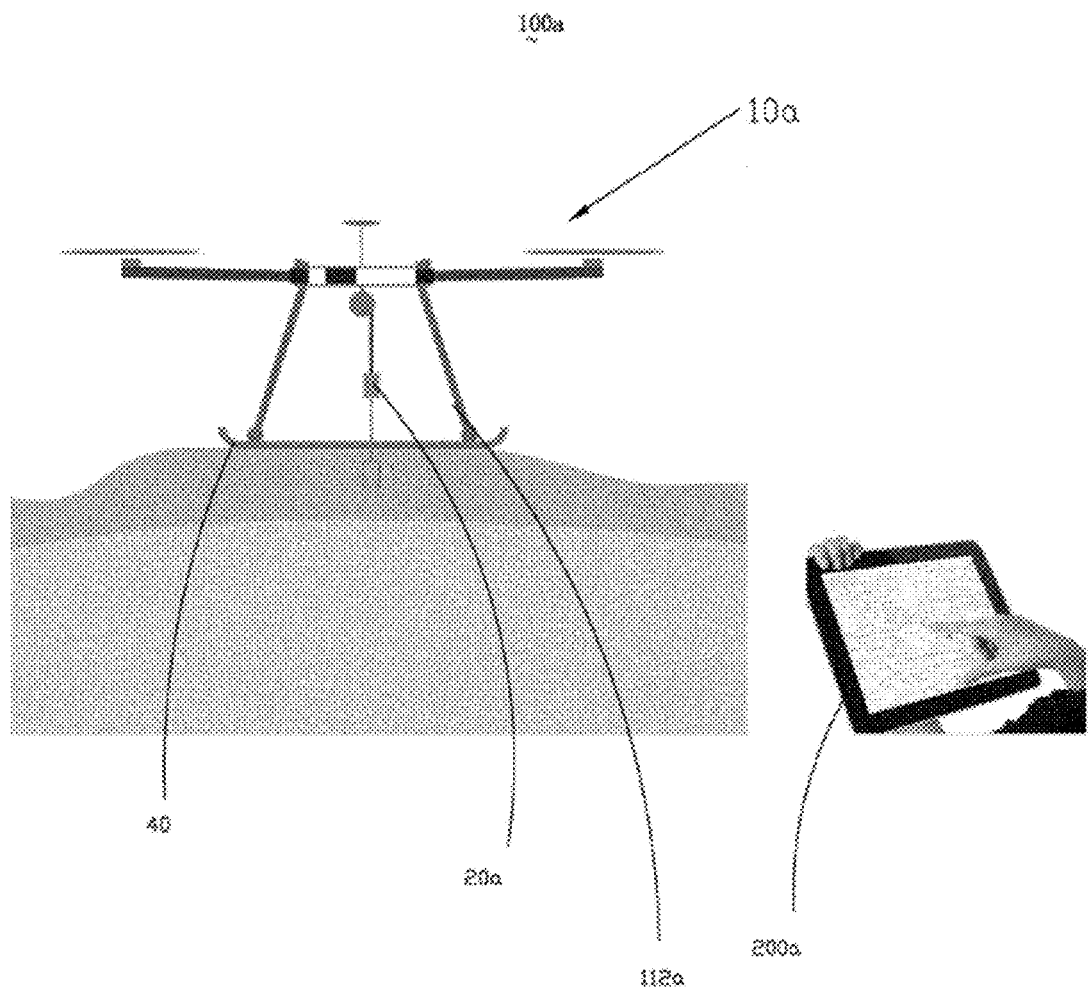
FIG. 5 is a use state diagram of a water sampling system according to the second implementation mode of the present disclosure.

Referring to FIG. 5, it illustrates a water sampling system 100a according to a second implementation mode of the present disclosure. The structure of the water sampling system 100a according to the second implementation mode is similar to that of the water sampling system 100 according to the first implementation mode, and their difference lies in that: the unmanned aerial vehicle 10a is provided thereon with a floating board 40. In this embodiment, the floating board 40 is fixedly arranged on the landing gears 112, and the floating board 40 is provided with a through opening to enable the water sampler 20a pass through. With the provision of the floating board 40, after the unmanned aerial vehicle 10a flies to the sampling site, the unmanned aerial vehicle 10a can float on a water surface using the floating board 40. In this implementation mode, as the unmanned aerial vehicle 10a floats on the water surface, it can be avoided that the water sampler 20a sways under the influence of the wind when descending in the air, thus reducing the risk that the water sampler 20a is damaged due to swaying.

It can be understood that the floating board 40 may also be connected to the unmanned aerial vehicle 10a through a connector, for example, a support frame, which is not limited to this embodiment.

Figure 6:
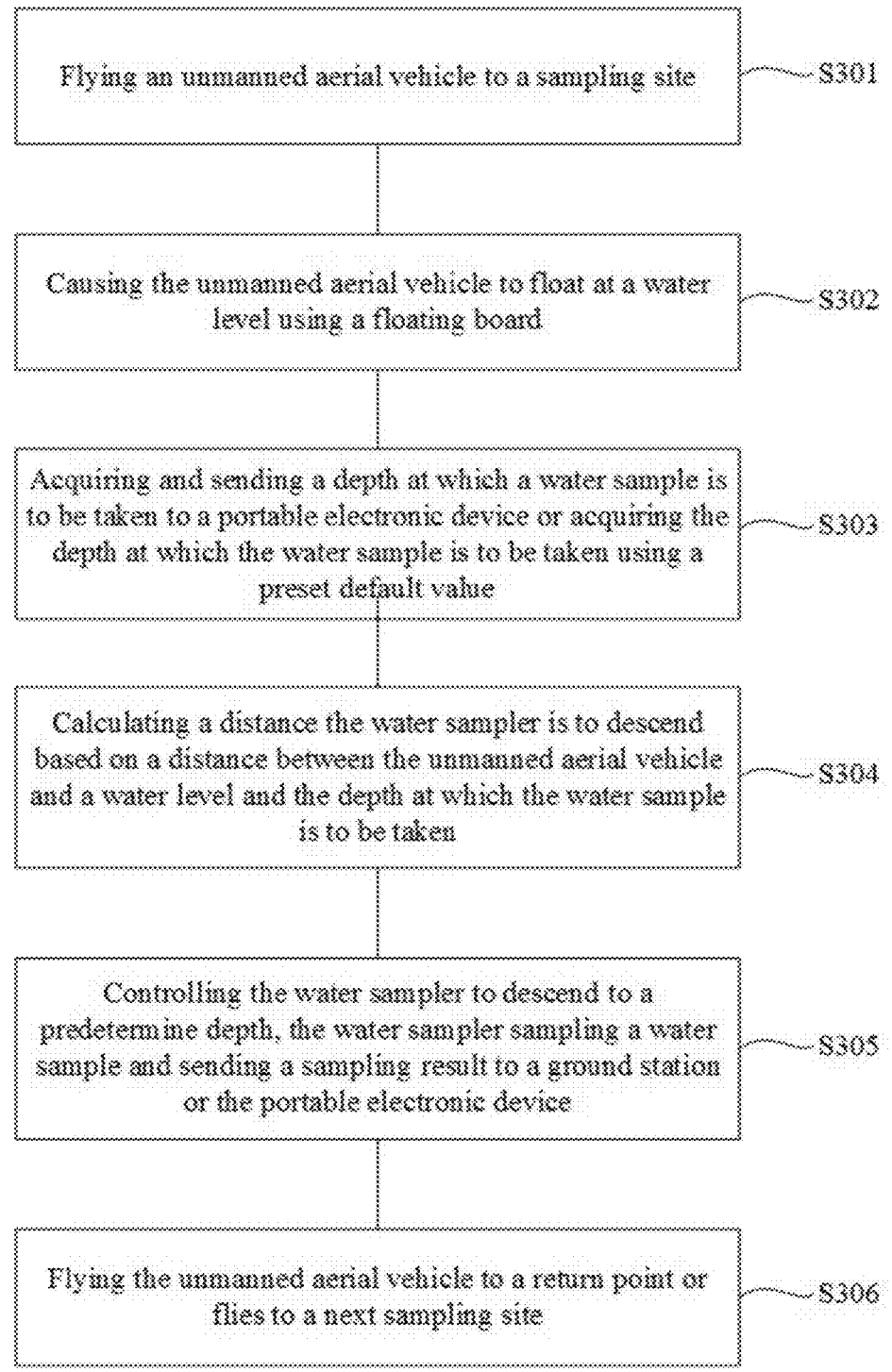
FIG. 6 is a flow chart of a water sampling method according to a third implementation mode of the present disclosure.

Referring to FIG. 6, a water sampling method according to a third implementation mode of the present disclosure includes the following steps:

S301: The unmanned aerial vehicle 10a flies to a sampling site.

S302: The unmanned aerial vehicle 10a floats on a water surface using a floating board 40.

A distance between the unmanned aerial vehicle 10a and a water surface is zero.

S303: A depth of a water sample to be taken is acquired from a portable electronic device, or the depth at which a water sample is to be taken is acquired using a preset default value.

S304: A distance the water sampler is to descend is calculated based on a distance between the unmanned aerial vehicle and a water surface and the depth at which the water sample is to be taken.

S305: The water sampler is controlled to descend to a predetermined depth, and the water sampler samples a water sample and sends a sampling result to a ground station or the portable electronic device.

S306: The unmanned aerial vehicle 10a flies to a return point or flies to a next sampling site.

Figure 7:
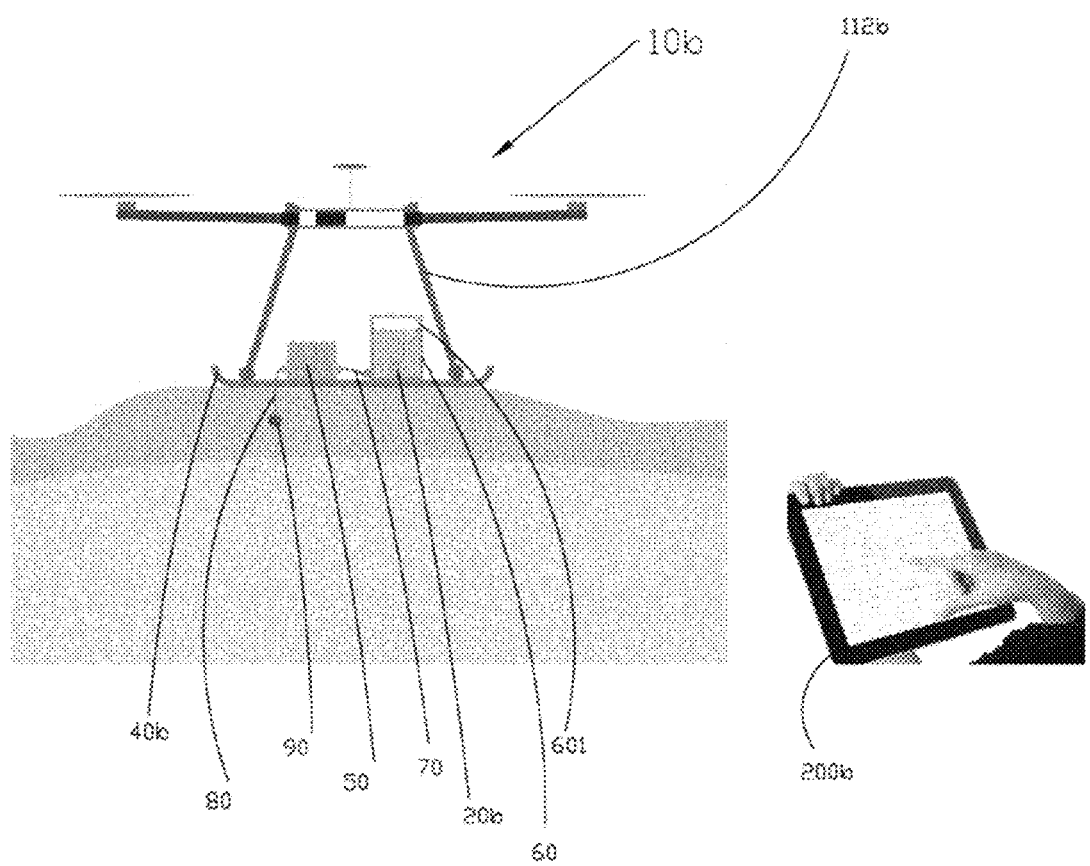
FIG. 7 is a use state diagram of a water sampling system according to the third implementation mode of the present disclosure.

Referring to FIG. 7, it illustrates a water sampling system 100b according to a third implementation mode of the present disclosure. The structure of the water sample sampling 100b according to the third implementation mode is similar to that of the water sampling system 100a according to the second implementation mode, and their difference lies in that: the floating board 40b of unmanned aerial vehicle 10b is provided thereon with a water pump 50, a reservoir 60, a first connecting pipe 70, a second connecting pipe 80, and a filter 90. The water sampler 20b is disposed in the reservoir 60 and is electrically connected with the main controller. The water pump 50 and the reservoir 60 are connected through the first connecting pipe 70. One end of the second connecting pipe 80 is connected to the water pump 50, and the other end is connected with the filter 90. In this embodiment, the water pump 50 is a peristaltic pump. The first connecting pipe 70 and the second connecting pipe 80 are both silicone tubes. The length of the second connecting pipe 80 is equal to the depth at which the water sample is to be taken. The filter 90 is used for filtering impurities. The reservoir 60 is provided with a water outlet 601 for overflowing the water to ensure freshness of the water quality.

The water sampler 20b is electrically connected with the main controller of the unmanned aerial vehicle 10b. The water sampler 20b sends a sampling result to the unmanned aerial vehicle 10b, and the unmanned aerial vehicle 10b, upon receipt of the sampling result, sends the sampling result to the portable electronic device 200b or a ground station.

Note that a wireless transmitting device can also be directly disposed on the water sampler 20b, and the sampling result may also be sent to the portable electronic device 200b or the ground station through the wireless transmitting device.

In this embodiment, the water pump 50 pumps water into the reservoir 60, and the water sampler 20b directly samples the water in the reservoir 60, so that the problem that the water sampler 20b can be smashed by rocks and damaged by extending below the water surface can be prevented.

In this embodiment, the floating board 40b is fixedly arranged on the landing gears 112b. In other embodiments, the floating board 40b may also be connected to the unmanned aerial vehicle 10b through a lifting device, and the lifting device descends the floating board 40b such that the floating board 40b floats at the water surface.

Figure 8:
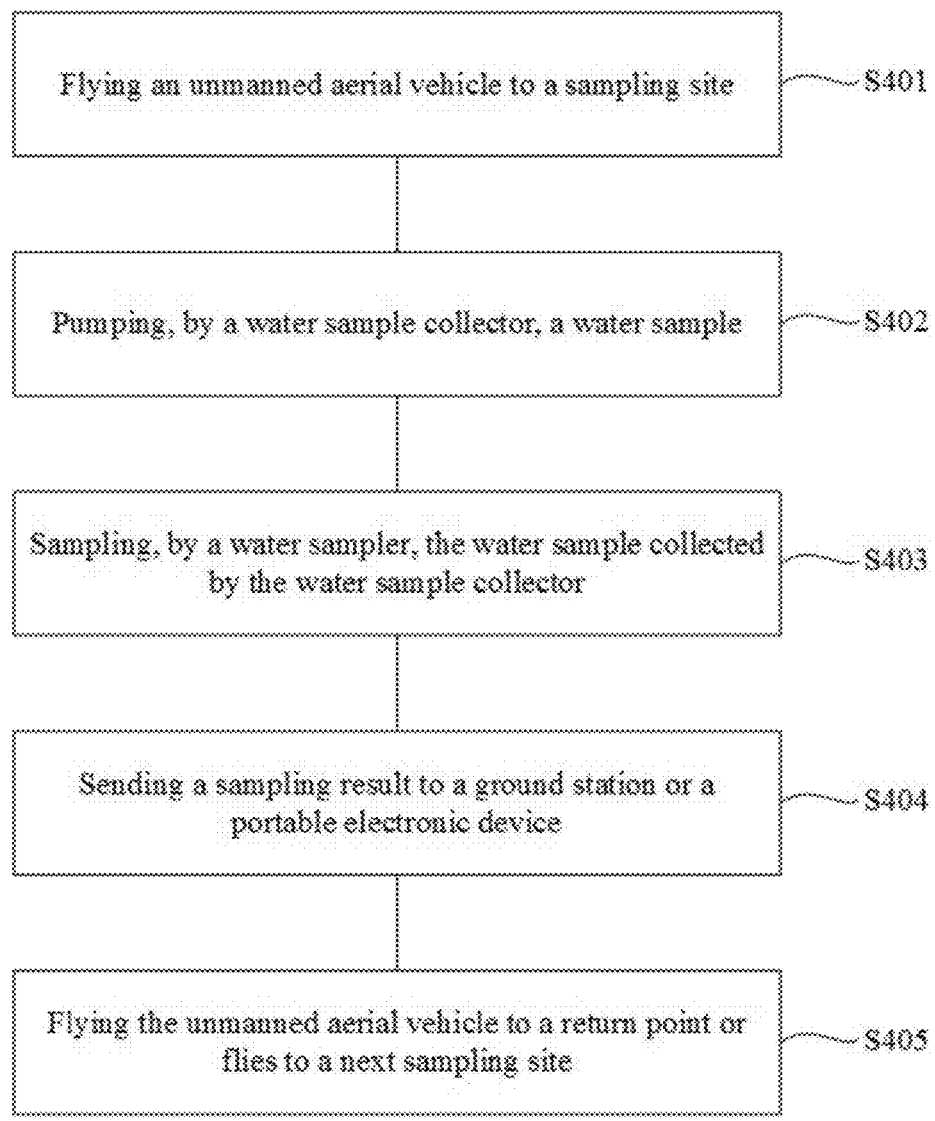
FIG. 8 is a flow chart of a water sampling method according to a fourth implementation mode of the present disclosure.

Referring to FIG. 8, a water sampling method according to a fourth implementation mode of the present disclosure includes the following steps:

S401: The unmanned aerial vehicle 10b flies to a sampling site.

S402: The water sample collector pumps a water sample.

When the floating board 40b is fixedly arranged on the landing gears 112b, the unmanned aerial vehicle 10b descends based on a distance between the unmanned aerial vehicle 10b and a water surface such that the floating board 40b floats at a water surface. The water pump 50 pumps a water sample to the reservoir 60. When the floating board 40b may also be connected to the unmanned aerial vehicle 10b through a lifting device, the pumping, by the water sample collector, of a water sample is accomplished through the following steps of:

based on a distance between the unmanned aerial vehicle 10b and a water surface, controlling, by the unmanned aerial vehicle 10b, the lifting device to descend the floating board 40b such that the floating board 40b floats at a water surface; and pumping, by the water pump 50, the water sample to the reservoir 60.

S403: The water sampler 20b samples the water sample pumped by the water sample collector.

The water sampler 20b samples the water quality in the reservoir 60.

S404: A sampling result is sent to a ground station or a portable electronic device 200b.

S405: The unmanned aerial vehicle 10b flies to a return point or flies to a next sampling site.

The above descriptions are merely embodiments of the present disclosure, but are not intended to limit the scope of the present disclosure. Any equivalent structure or equivalent process variation made by using contents of the specification and the drawings of the present disclosure, or directly or indirectly applied to other related technical fields, should be likewise included in the scope of the present disclosure.

What is claimed is:

1. A water sampling method comprising:
controlling an unmanned aerial vehicle hovering above a water surface of a sampling site;
acquiring, by the unmanned aerial vehicle, a sampling depth at which a water sample is to be taken, the sampling depth being sent by a portable electronic device or being a preset default depth;
calculating a descending distance based on a sum of the sampling depth and a distance between a bottom of the unmanned aerial vehicle and the water surface;
controlling the water sampler to descend for the descending distance;
sampling, by the water sampler, a water sample; and
sending a sampling result to a ground station or the portable electronic device.

2. The water sampling method according to claim 1, further comprising:
receiving, by the unmanned aerial vehicle, position information of the sampling site; and
flying to the sampling site based on the position information of the sampling site.

3. The water sampling method according to claim 2, wherein receiving the position information of the sampling site includes receiving the position information of the sampling site sent by the portable electronic device selected from a satellite map displayed on the portable electronic device or input into the portable electronic device.

4. The water sampling method according to claim 1, further comprising:
flying to the sampling site under a control of a remote controller.

5. The water sampling method according to claim 1, wherein acquiring the sampling depth includes acquiring a depth value input into the portable electronic device and sent by the portable electronic device to the unmanned aerial vehicle.

6. The water sampling method according to claim 1, further comprising:
floating on the water surface through a floating board attached to the unmanned aerial vehicle, such that the distance between the bottom of the unmanned aerial vehicle and the water surface is zero.

7. The water sampling method according to claim 1, wherein the preset default depth is about 0.4 m to about 1 m underwater.

8. The water sampling method according to claim 1, further comprising:

measuring, by a distance sensor attached to the unmanned aerial vehicle, the distance between the bottom of the unmanned aerial vehicle and the water surface.

9. The water sampling method according to claim 8, wherein the distance sensor is an ultrasonic sensor or a barometer.

10. The water sampling method according to claim 1, further comprising:
controlling a lifting device to drive the water sampler to descend by the descending distance.

11. A water sampling system comprising:
an unmanned aerial vehicle; and
a water sampler coupled to the unmanned aerial vehicle, and configured to ascend and descend relative to the unmanned aerial vehicle and to sample a water sample,
wherein the unmanned aerial vehicle is configured to:
hover above a water surface of a sampling site,
acquire a sampling depth at which a water sample is to be taken, the sampling depth being sent by a portable electronic device or being a preset default depth,
calculate a descending distance based on a sum of the sampling depth and a distance between a bottom of the unmanned aerial vehicle and the water surface, and
control the water sampler to descend for the descending distance.

12. The water sampling system according to claim 11, wherein:
the unmanned aerial vehicle comprises a signal transceiver configured to receive position information of the sampling site,
the unmanned aerial vehicle is further configured to fly to the sampling site based on the position information of the sampling site, and
the signal transceiver is further configured to send a sampling result to the portable electronic device or a ground station.

13. The water sampling system according to claim 12, wherein the signal transceiver is configured to receive the position information of the sampling site sent by the portable electronic device selected from a satellite map displayed on the portable electronic device or input into the portable electronic device.

14. The water sampling system according to claim 12, wherein:
the signal transceiver is further configured to receive a control signal from a remote controller, and
the unmanned aerial vehicle is configured to fly to the sampling site under a control of the remote controller.

15. The water sampling system according to claim 11, wherein the transceiver is further configured to receive a depth value input into and sent by the portable electronic device as the sampling depth at which the water sample is to be taken.

16. The water sampling system according to claim 11, wherein:
the unmanned aerial vehicle comprises a floating board, and
the unmanned aerial vehicle is configured to float on the water surface through the floating board, such that the distance between the bottom of the unmanned aerial vehicle and the water surface is zero.

17. The water sampling system according to claim 11, wherein the preset default depth is about 0.4 m to about 1 m underwater.

18. The water sampling system according to claim 11, wherein the unmanned aerial vehicle comprises a distance sensor configured to measure the distance between the unmanned aerial and the water surface.

19. The water sampling system according to claim 18, wherein the distance sensor is an ultrasonic sensor or a barometer.

20. The water sampling system according to claim 11, wherein:
the unmanned aerial vehicle further comprises a lifting device configured to drive the water sampler to ascend or descend relative to the unmanned aerial vehicle, and
the unmanned aerial vehicle is further configured to control the lifting device to drive the water sampler to descend by the descending distance.

* * * * *